United States Patent
Tsubuku et al.

(10) Patent No.: US 11,399,859 B2
(45) Date of Patent: Aug. 2, 2022

(54) ENERGY CONTROL DEVICE AND TREATMENT SYSTEM

(71) Applicant: OLYMPUS CORPORATION, Hachioji (JP)

(72) Inventors: Yoshihiro Tsubuku, Fuchu (JP); Minoru Kawasaki, Tokyo (JP); Gen Kato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 712 days.

(21) Appl. No.: 16/299,482

(22) Filed: Mar. 12, 2019

(65) Prior Publication Data
US 2019/0209202 A1  Jul. 11, 2019

Related U.S. Application Data

(63) Continuation of application No. PCT/JP2016/076860, filed on Sep. 12, 2016.

(51) Int. Cl.
*A61B 17/32* (2006.01)
*A61B 17/00* (2006.01)
(Continued)

(52) U.S. Cl.
CPC ...... *A61B 17/320092* (2013.01); *A61B 90/90* (2016.02); *A61B 2017/0003* (2013.01);
(Continued)

(58) Field of Classification Search
CPC .. A61B 17/320092; A61B 2017/00017; A61B 2017/00367; A61B 2017/320071;
(Continued)

(56) References Cited

U.S. PATENT DOCUMENTS

| 2010/0168742 A1 | 7/2010 | Shibata |
| 2013/0066238 A1 | 3/2013 | Irisawa et al. |
| 2017/0079678 A1 | 3/2017 | Ishikawa |

FOREIGN PATENT DOCUMENTS

| JP | 2006-288431 A | 10/2006 |
| WO | 2010/076869 A1 | 7/2010 |

(Continued)

OTHER PUBLICATIONS

Oct. 25, 2016 International Search Report issued in International Patent Application No. PCT/JP2016/076860.
(Continued)

*Primary Examiner* — Diane D Yabut
(74) *Attorney, Agent, or Firm* — Oliff PLC (57) ABSTRACT

An energy control device for an ultrasonic treatment tool which includes an ultrasonic transducer and an end effector that performs a treatment using the ultrasonic vibration generated by the ultrasonic transducer comprises a first power supply configured to supply an electric power to the ultrasonic transducer, and a circuit. The circuit is configured to measure an output duration, monitor a characteristic parameter representing a situation of the treatment, set a time threshold value based on the characteristic parameter, and perform, when the output duration exceeds the time threshold value, at least one of: stopping or reducing the output of electric power from the first power supply to the ultrasonic transducer and notifying that the output duration has exceeded the time threshold value.

20 Claims, 8 Drawing Sheets

(51) Int. Cl.
    *A61B 90/00*        (2016.01)
    *A61B 90/90*        (2016.01)
(52) U.S. Cl.
    CPC .............. *A61B 2017/00017* (2013.01); *A61B 2017/00367* (2013.01); *A61B 2017/320071* (2017.08); *A61B 2017/320082* (2017.08); *A61B 2017/320094* (2017.08); *A61B 2090/064* (2016.02)
(58) Field of Classification Search
    CPC ......... A61B 2017/320082; A61B 2017/00128; A61B 2017/00132; A61B 2017/00022; A61B 2017/00026; A61B 2017/0003; A61B 2017/00039; A61B 2017/00106; A61B 2017/0011; A61B 2017/0015; A61B 2017/00119; A61B 2017/00123; A61B 18/1445; A61B 2018/00702; A61B 2018/00886; A61B 2018/00636; A61B 2018/00642; A61B 2018/00648; A61B 2018/00666; A61B 2018/00696; A61B 2018/00708; A61B 2018/00726; A61B 2018/00732; A61B 2018/0072; A61B 2018/00773; A61B 2018/00779; A61B 2018/0088
    See application file for complete search history.

(56) References Cited

FOREIGN PATENT DOCUMENTS

| | | |
|---|---|---|
| WO | 2012/108295 A1 | 8/2012 |
| WO | 2015/122306 A1 | 8/2015 |
| WO | 2016/132835 A1 | 8/2016 |

OTHER PUBLICATIONS

Jan. 26, 2021 Office Action issued in Japanese Patent Application No. 2020-070156.
Mar. 12, 2019 International Preliminary Report on Patentability issued in International PCT/JP2016/076860.

| EXAMPLE OF X \ VALUE OF X | X<X2 | X2≦X≦X1 | X>X1 |
|---|---|---|---|
| ULTRASONIC VIBRATION AMPLITUDE (ULTRASONIC CURRENT) | Tth2 INCREASE | Tave | Tth2 DECREASE |
| GRIPPING AMOUNT OF HANDLE | Tth2 INCREASE | Tave | Tth2 DECREASE |
| AMOUNT OF TISSUE-GRASPING FORCE | Tth2 INCREASE | Tave | Tth2 DECREASE |
| INITIAL VALUE OF TISSUE IMPEDANCE | Tth2 INCREASE | Tave | Tth2 DECREASE |

ENERGY CONTROL DEVICE AND TREATMENT SYSTEM

CROSS-REFERENCE TO RELATED APPLICATIONS

This application is a Continuation Application of PCT Application No. PCT/JP2016/076860, filed Sep. 12, 2016, the entire contents of which are incorporated herein by reference.

BACKGROUND OF THE INVENTION

1. Field of the Invention

The present invention relates to an energy control device for an ultrasonic treatment tool and a treatment system comprising the same.

2. Description of the Related Art

Known have been ultrasonic treatment tools having a pair of grasping pieces for grasping living tissue to be treated, one of the grasping pieces vibrating ultrasonically to promote coagulation, incision or the like of the living tissue being grasped. Continued vibration of the grasping pieces of this kind of ultrasonic treatment tools despite the treatment being completed and the living tissue being successfully incised is undesired. Vibration of the grasping pieces while in direct mutual contact may cause damage to the grasping pieces.

An example of such ultrasonic treatment tool is disclosed in International Publication No. 2015/122306. In this ultrasonic treatment tool, completion of the treatment is detected as follows. That is, electrical impedance of an ultrasonic transducer of the ultrasonic treatment tool is obtained. This impedance gradually increases and then gradually decreases. The ultrasonic treatment tool detects an excision of the grasped living tissue based on the impedance variation and adjusts the output.

BRIEF SUMMARY OF THE INVENTION

According to an aspect of the invention, an energy control device provides an electric power to an ultrasonic treatment tool. The ultrasonic treatment tool comprises an ultrasonic transducer that generates an ultrasonic vibration by being supplied with the electric power and an end effector that performs a treatment using the ultrasonic vibration generated by the ultrasonic transducer. The energy control device comprises a first power supply configured to supply the electric power to the ultrasonic transducer, and at least one circuit. The circuit is configured to measure an output duration related to a time during which the first power supply continues outputting, monitor a predetermined characteristic parameter representing a situation of the treatment, set a time threshold value based on the characteristic parameter, wherein the time threshold value is set sequentially based on the characteristic parameter monitored repeatedly until the output duration exceeds the time threshold value, and perform, when the output duration exceeds the time threshold value, at least one of: stopping or reducing the output of electric power from the first power supply to the ultrasonic transducer and notifying that the output duration has exceeded the time threshold value.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

A first embodiment of the present invention will be described with reference to the drawings. The first embodiment relates to a treatment system for treating living tissue using ultrasonic vibration.

Treatment System Configuration

Figure 1:
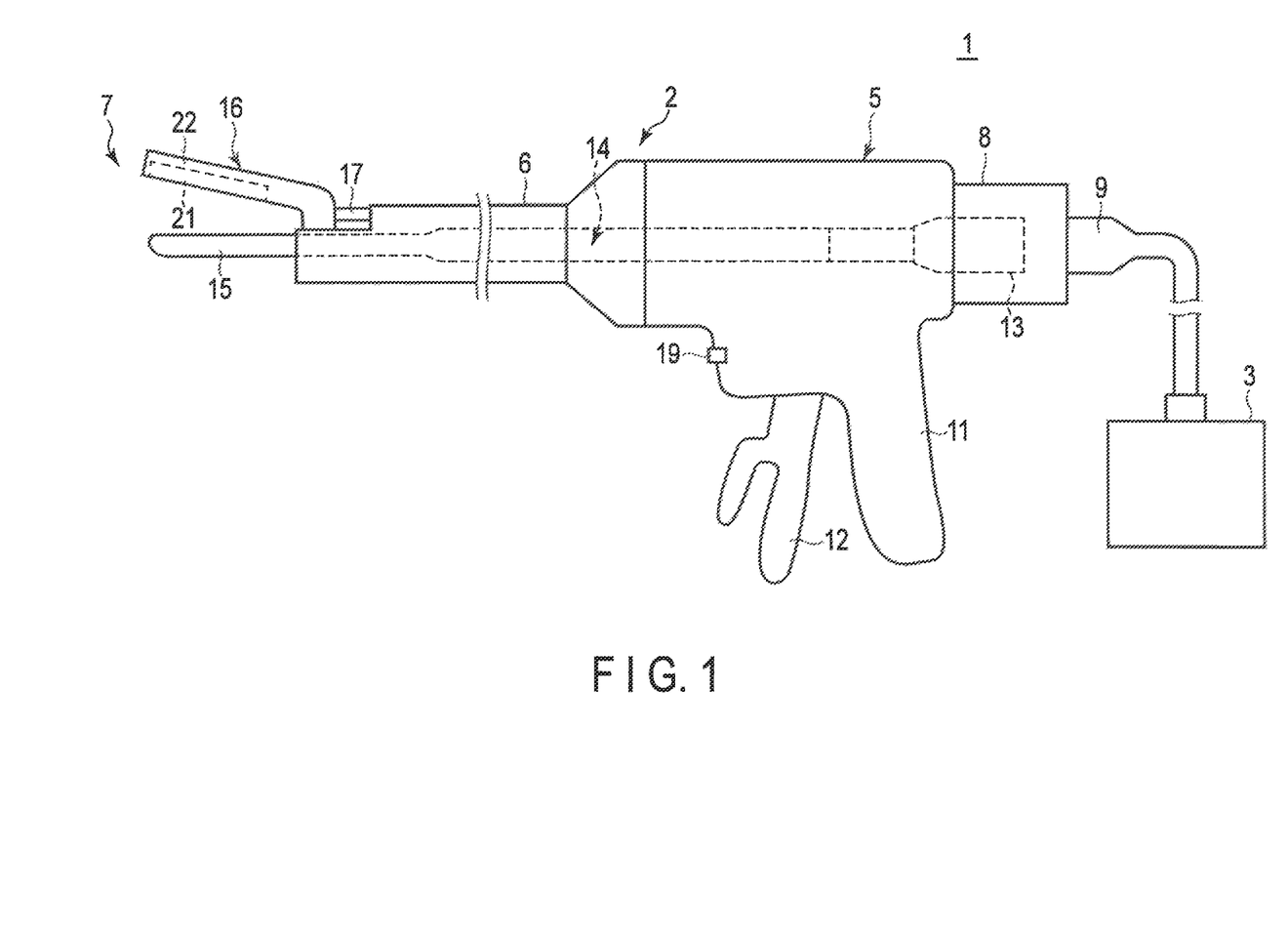
FIG. 1 is a schematic view of an example of a treatment system according to a first embodiment.

FIG. 1 is a schematic view showing a treatment system 1. As shown in FIG. 1, the treatment system 1 comprises an ultrasonic treatment tool 2 and an energy control device 3 that supplies power to the ultrasonic treatment tool 2.

The ultrasonic treatment tool 2 comprises a housing 5, a shaft 6 connected to the housing 5, and an end effector 7 provided at the end of the shaft 6. The side on which the end effector 7 is provided will be referred to as the distal end side and the side on which the housing 5 is provided will be referred to as the proximal end side. The housing 5 is provided with a grip 11 so that a user can hold the ultrasonic treatment tool 2, and a handle 12 that is opened and closed with respect to the grip 11.

On the proximal end side of the housing 5, an ultrasonic transducer unit 8 is provided. The ultrasonic transducer unit 8 has an ultrasonic transducer 13 including at least one piezoelectric element. The ultrasonic transducer unit 8 is detachably connected to the energy control device 3 via a cable 9. AC power is supplied from the energy control device 3 to the ultrasonic transducer 13 of the ultrasonic transducer unit 8, thereby causing the ultrasonic transducer 13 to vibrate.

A rod member 14 is connected to the ultrasonic transducer 13. The rod member 14 passes through the inside of the housing 5 and the shaft 6 and reaches the end effector 7. That is, the distal end portion of the rod member 14 constitutes a first grasping piece 15 of the end effector 7. The rod member 14 is formed of a material having a high vibration transmission property such as a titanium alloy. The ultrasonic vibration generated by the ultrasonic transducer 13 is transmitted to the rod member 14. As a result, the first grasping piece 15 vibrates. The first grasping piece 15 vibrates at a resonance frequency of the vibration system that is designed arbitrarily. The frequency of this resonance is not limited to this, and may, for example, be approximately several tens of kHz, for example, equal to or greater than 46 kHz and equal to or less than 48 kHz (approximately 47 kHz).

A second grasping piece 16 is attached to the distal end portion of the shaft 6 that is opened and closed with respect to the first grasping piece 15. The second grasping piece 16 and the handle 12 are connected by a movable member 17 passing inside the shaft 6. By opening or closing the handle 12 with respect to the grip 11, the movable member 17 moves to the distal end side or the proximal end side, and the second grasping piece 16 rotates with respect to the shaft 6 to open or close with respect to the first grasping piece 15. In this manner, the opening and closing operations of the handle 12 with respect to the grip 11 causes the first grasping piece 15 and the second grasping piece 16 of the end effector 7 to open and close. The end effector 7 is configured to grip the living tissue to be treated by the first grasping piece 15 and the second grasping piece 16 constituting a pair of grasping pieces.

The second grasping piece 16 comprises a pad member 21 and a holder member 22 to which the pad member 21 is attached. The pad member 21 is formed of a resin such as polytetrafluoroethylene (PTFE). When the first grasping piece 15 and the second grasping piece 16 close, the pad member 21 of the second grasping piece 16 comes into contact with the first grasping piece 15, while the other regions of the second grasping piece 16 do not come into contact with the first grasping piece 15.

Figure 2A:
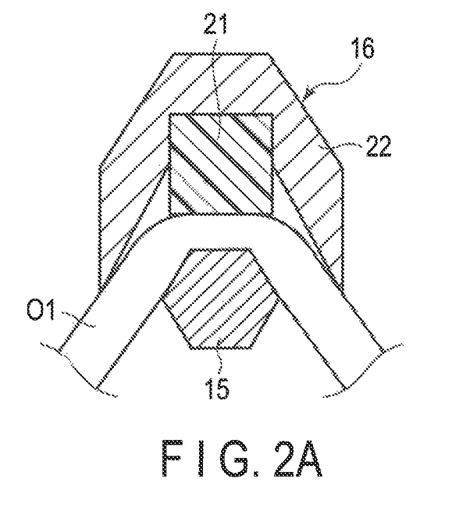
FIG. 2A is a schematic view showing a cross section of an end effector and the tissue to be treated according to the first embodiment, the cross section being perpendicular to the longitudinal axis of the end effector.
Figure 2B:
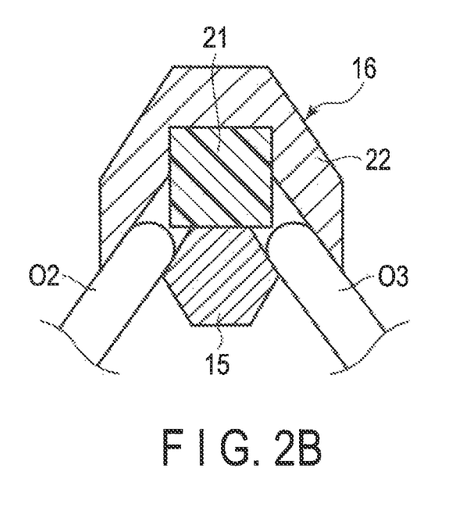
FIG. 2B is a schematic view showing a cross section of the end effector and the tissue to be treated according to the first embodiment, in a state in which the tissue is incised, the cross section being perpendicular to the longitudinal axis of the end effector.

FIGS. 2A and 2B are views showing a cross section perpendicular to the longitudinal axes of the first grasping piece 15 and the second grasping piece 16 when using the ultrasonic treatment tool 2. FIG. 2A shows a state in which a tissue O1 to be treated is sandwiched between the first grasping piece 15 and the second grasping piece 16. While sandwiching the tissue O1 between the first grasping piece 15 and the second grasping piece 16, the ultrasonic treatment tool 2 can incise the tissue O1 and at the same time promote coagulation of the same by the ultrasonic vibration from the first grasping piece 15. FIG. 2B shows a state in which the tissue is incised into a first tissue piece O2 and a second tissue piece O3. At this moment, the pad member 21 is in contact with the first grasping piece 15.

As shown in FIG. 1, the housing 5 is provided with an operating button 19. The operating button 19 is actuated to switch the supply of electric power from the energy control device 3 to the ultrasonic transducer unit 8 on or off. The treatment system 1 may be provided with a foot switch having the same function as the operating button 19 instead of or together with the operating button 19.

Figure 3:
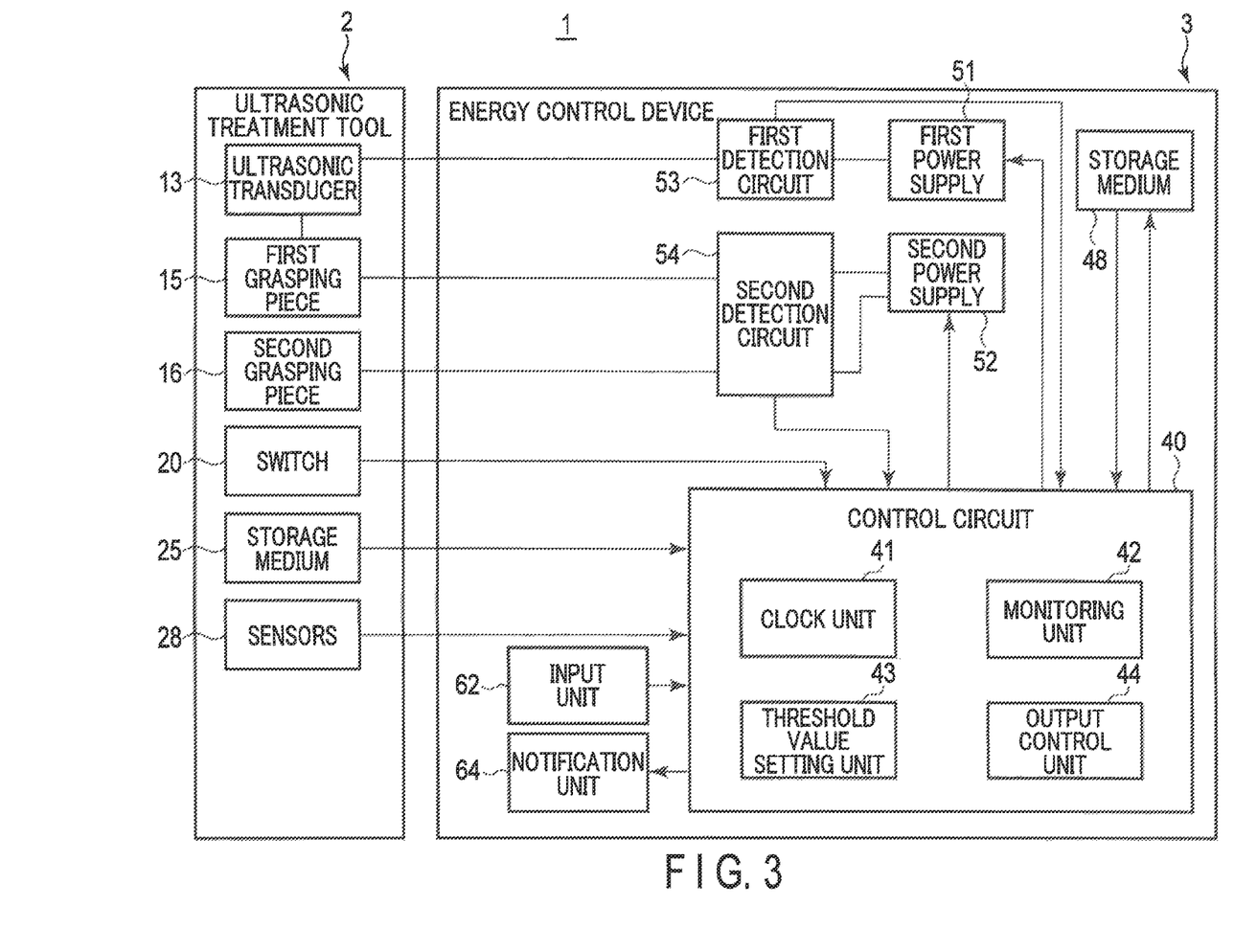
FIG. 3 is a schematic block diagram showing an example of a configuration of the treatment system according to the first embodiment.

FIG. 3 is a schematic diagram showing an example of a configuration of the treatment system 1 pertaining to the supply of electric power from the energy control device 3 to the ultrasonic treatment tool 2.

As described above, the ultrasonic treatment tool 2 is provided with the ultrasonic transducer 13, the first grasping piece 15, and the second grasping piece 16. The ultrasonic treatment tool 2 is further provided with a switch 20 and a storage medium 25 as shown in FIG. 3, The ultrasonic transducer 13 is an ultrasonic transducer as a vibration source provided in the ultrasonic transducer unit 8 described above. The switch 20 is provided inside the housing 5 of the ultrasonic treatment tool 2. By actuating the operating button 19, the switch 20 is switched on or off. The storage medium 25 stores information on the treatment tool. The ultrasonic treatment tool 2 is provided as needed with various sensors 28. The sensors 28 may, for example, be sensors for detecting the amount with which the handle 12 is being gripped, indicative of the amount of displacement of the handle 12. This gripping amount is represented, for example, by the amount of displacement of the handle 12 from the most open position with respect to the grip 11. The sensors 28 may further be sensors for detecting the amount of force with which the tissue is being grasped, indicative of the force with which the living tissue to be treated is being grasped by the first grasping piece 15 and by the second grasping piece 16.

The energy control device 3 comprises a control circuit 40 for controlling the operations of the treatment system 1, and a storage medium 48. The control circuit 40 operates based on, for example, a program stored in the storage medium 48 to control the operations of each part of the energy control device 3. Stored in the storage medium 48 are a processing program used in the control circuit 40, parameters and tables used for calculations performed in the control circuit 40, and the like.

The energy control device 3 further comprises a first power supply 51. Under the control of the control circuit 40, the first power supply 51 supplies AC power to the ultrasonic transducer 13 of the ultrasonic treatment tool 2, a frequency of the AC power corresponding to ultrasonic frequency. The electric power supplied from the first power supply 51 causes the ultrasonic transducer 13 to vibrate at the resonant frequency, whereby the first grasping piece 15 vibrates at a frequency in the ultrasonic range to treat the living tissue with which the first grasping piece 15 is in contact.

The energy control device 3 may further comprise a second power supply 52. The second power supply 52 applies a predetermined voltage between the first grasping piece 15 and the second grasping piece 16 under the control of the control circuit 40. When the output from the second power supply 52 is a sufficiently strong high-frequency power output, a high-frequency current flows into the living tissue that is grasped between the first grasping piece 15 and the second grasping piece 16, by which the living tissue can be treated by a Joule heat generated in the living tissue. The second power supply 52 may be configured to output an energy small enough to measure the impedance between the first grasping piece 15 and the second grasping piece 16.

The energy control device 3 comprises a first detection circuit 53. The first detection circuit 53 comprises a voltage detection circuit, a current detection circuit, and an A/D converter. The first detection circuit 53 detects the output voltage and the output current of the first power supply 51 and transmits the detection result to the control circuit 40 as a digital signal. The control circuit 40 controls the output of the first power supply 51 based on the voltage value and the current value detected by the first detection circuit 53, the impedance value calculated therefrom, and the like.

The energy control device 3 may further comprise a second detection circuit 54. The second detection circuit 54 comprises a voltage detection circuit, a current detection circuit, and an A/D converter. The second detection circuit 54 detects the output voltage and the output current of the second power supply 52 and transmits the detection result to the control circuit 40 as a digital signal. The control circuit 40 can calculate the impedance value of the living tissue grasped between the first grasping piece 15 and the second grasping piece 16 based on the voltage value and the current value detected by the second detection circuit 54. The calculated impedance value is used for controlling the outputs of the first power supply 51 and the second power supply 52. The second detection circuit 54 may detect the output voltage and the output current which is related to the output of the second power supply 52 that outputs the high frequency power for treating the living tissue grasped by the end effector 7. The second detection circuit 54 may further detect the output voltage and the output current which is related to the output of the second power supply 52 that outputs a weak power for measuring the impedance of the living tissue grasped by the end effector 7.

The energy control device 3 further comprises an input unit 62 and a notification unit 64. The input unit 62 is a unit that receives an input by the user to the energy control device 3. The input unit 62 includes, for example, a touch panel, a button switch, a keyboard, or the like. The notification unit 64 is a unit for announcing information to the user. The notification unit 64 includes, for example, a display or a speaker.

The energy control device 3 according to the first embodiment performs the following operations. When the switch 20 of the ultrasonic treatment tool 2 is switched on, the energy control device 3 detects this and starts supplying the electric power to the ultrasonic treatment tool 2. Subsequently, the energy control device 3 measures the duration of treatment, that is, the duration of power supply from the start, and after a predetermined time has elapsed, it determines that the treatment has completed, at which point it puts out a notification that the output has been stopped or reduced, that the treatment has been completed or the like. The control circuit 40 performs calculations related to these operations of the energy control device 3.

The control circuit 40 comprises a clock unit 41, a monitoring unit 42, a threshold value setting unit 43, and an output control unit 44. The clock unit 41 measures the output duration related to the time during which the first power supply 51 continues to output. In the first embodiment, the duration of output from the time that the first power supply 51 began outputting is measured as the output duration.

The monitoring unit 42 monitors a predetermined characteristic parameter. Such a characteristic parameter may be the current supplied from the first power supply 51 to the ultrasonic transducer 13 (referred to as ultrasonic current), correlating with the vibration amplitude of the ultrasonic transducer 13, namely the amplitude of the first grasping piece 15. Such a characteristic parameter may further be the amount with which the handle 12 is being gripped, obtained by the sensors 28 of the ultrasonic treatment tool 2. Such a characteristic parameter may even further be the amount of force with which the living tissue is being grasped by the first grasping piece 15 and by the second grasping piece 16, obtained by the sensors 28 of the ultrasonic treatment tool 2. Such a characteristic parameter may yet even further be the initial value or the like, of, for example, the impedance value between the first grasping piece 15 and the second grasping piece 16 calculated from the current value and the voltage value detected by the second detection circuit 54, that is, the impedance value related to the living tissue.

The threshold value setting unit 43 sets a time threshold value being a threshold value related to the time measured by the clock unit 41 based on the characteristic parameter. The output control unit 44 controls the outputs of the first power supply 51 and the second power supply 52. In particular, when the output duration measured by the clock unit 41 exceeds the time threshold value set by the threshold value setting unit 43, the output control unit 44 stops the output of power to the ultrasonic transducer 13 from the first power supply 51. The output control unit 44 may, instead of stopping the output, reduce the output or notify, by using the notification unit 64, the user of the circumstance that the output duration has exceeded the time threshold value.

The control circuit 40 includes an integrated circuit such as a central processing unit (CPU), an application specific integrated circuit (ASIC), or a field programmable gate array (FPGA). The control circuit 40 may be constituted by a single integrated circuit or the like, or a combination of a plurality of integrated circuits or the like. The operations of these integrated circuits are performed by a program recorded in, for example, the storage medium 48 or in a recording area in the integrated circuit.

Treatment System Operations

The operations of the treatment system 1 according to the first embodiment will be described. When treating the treatment target such as living tissue by using the treatment system 1, the user holds the grip 11 and the handle 12, and inserts the end effector 7 into a body cavity such as an abdominal cavity or the like. The user places the treatment target such as living tissue between the first grasping piece 15 and the second grasping piece 16, and closes the handle 12 with respect to the grip 11. As a result, the second grasping piece 16 is closed with respect to the first grasping piece 15, and the living tissue is grasped between the first grasping piece 15 and the second grasping piece 16.

In this state, the user switches on the operating button 19. At this point, the control circuit 40 detects that the switch 20 has been switched on. The output control unit 44 of the control circuit 40 causes the first power supply 51 to start outputting power. The first power supply 51 supplies the power to the ultrasonic transducer 13 under the control of the control circuit 40. As a result, the ultrasonic transducer 13 generates ultrasonic vibration and the generated ultrasonic vibration is transmitted to the first grasping piece 15 via the rod member 14. When the first grasping piece 15 starts ultrasonically vibrating while the tissue to be treated is being grasped between the first grasping piece 15 and the second grasping piece 16, frictional heat is being generated between the first grasping piece 15 and the tissue being grasped. The frictional heat denatures the protein in the living tissue, thereby both promoting coagulation of the living tissue and incising the living tissue.

The control circuit 40 may further cause the second power supply 52 to output power together with the first power supply 51, when the energy control device 3 has the second power supply 52 that outputs the high-frequency power. In that case, under the control of the control circuit 40, the second power supply 52 applies a high-frequency voltage between the first grasping piece 15 and the second grasping piece 16. As a result, a high-frequency current flows through the living tissue grasped between the first grasping piece 15 and the second grasping piece 16. By this high frequency current, a Joule heat is generated in the living tissue. This heat also promotes coagulation of the living tissue.

When the tissue to be treated has been incised, the first grasping piece 15 and the second grasping piece 16 are in contact, as shown in FIG. 2B. In this state, the pad member 21 of the second grasping piece 16 or the like may suffer damage when the first grasping piece 15 continues vibrating ultrasonically. Therefore, in the first embodiment, the control circuit 40 estimates the point in time at which the tissue will be incised. Based on the time during which the treatment is being performed, that is, based on the elapsed time since the first power supply 51 began outputting power, the control circuit 40 causes to stop the supply of electric power to the ultrasonic transducer 13 or to be decreased, or it notifies the user that the tissue has presumably been incised.

Output Control Process

Figure 4:
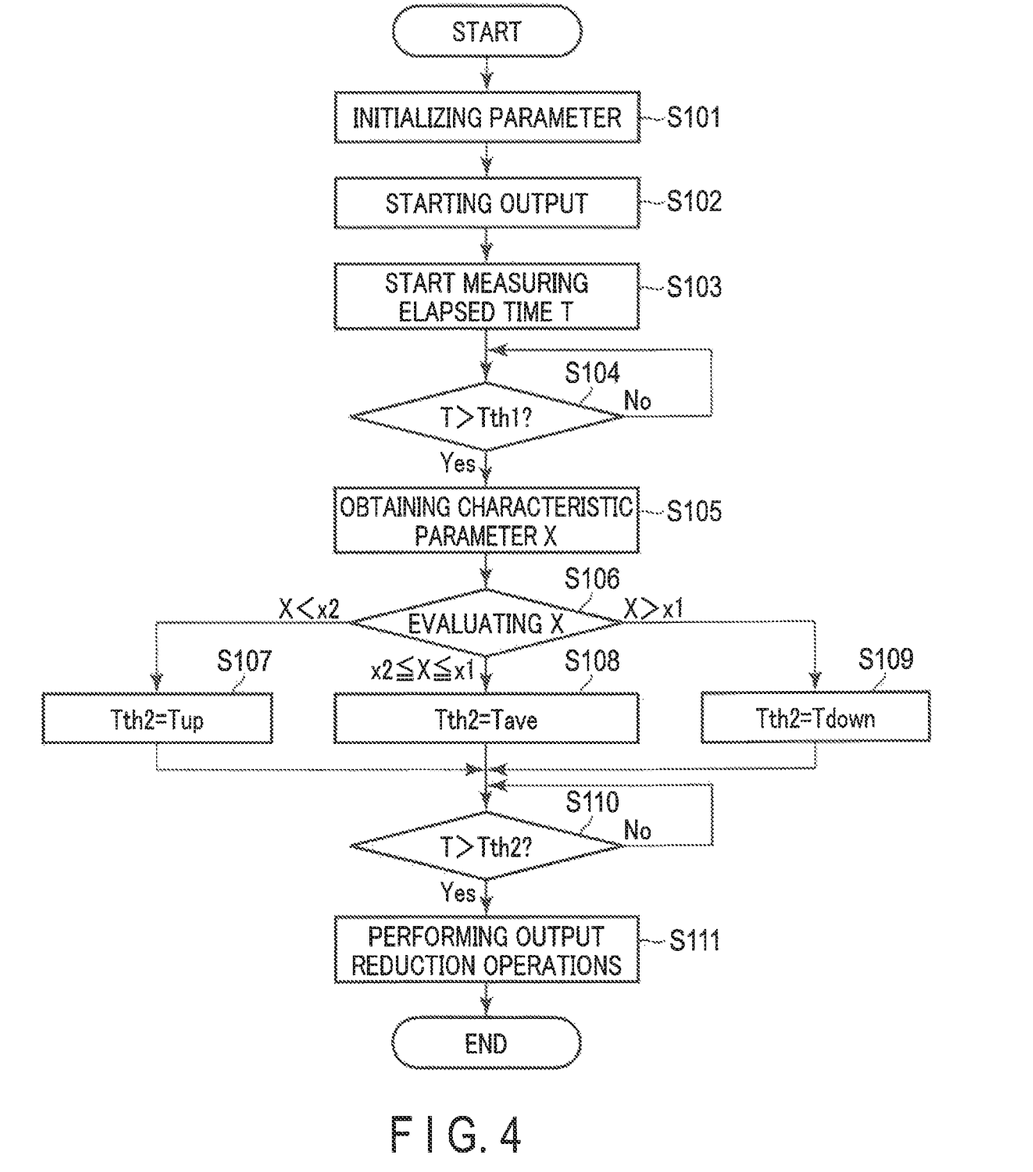
FIG. 4 is a schematic flowchart showing an example of an output control process according to the first embodiment.

The output control performed by the control circuit 40 will be described with reference to the flowchart shown in FIG. 4. The output control process shown in FIG. 4 starts when, for example, the user pushes the operating button 19.

In step S101, the control circuit 40 initializes the various parameters. For example, the parameter T representing the elapsed time of the treatment is set to 0, and the second time threshold value Tth2 indicative of the timing at which to reduce the output is set to Tave, namely the standard value.

In step S102, the output control unit 44 of the control circuit 40 causes the first power supply 51 to start outputting power. Under the control of the control circuit 40, the first power supply 51 supplies a predetermined power to the ultrasonic transducer 13. As a result, the first grasping piece 15 vibrates at a frequency in the ultrasonic range to perform the living tissue treatment. In step S103, the clock unit 41 of the control circuit 40 starts measuring the elapsed time T of the treatment. That is, the clock unit 41 starts counting the parameter T. Using the elapsed time T, the continued duration of power output by the first power supply 51 since the output began is measured.

Generally, when performing a treatment, the temperature of the first grasping piece 15 increases gradually and the state of the living tissue contacting the first grasping piece 15 also changes, so that the resonant frequency of the first grasping piece 15 changes. The control circuit 40 thus causes the first power supply 51 to scan the output frequency, and then start controlling for which the phase-locked loop (PLL) is used for causing the first power supply 51 to output electric power. That is, the output control unit 44 of the control circuit 40 causes the first power supply 51 to output power while gradually changing the output frequency, for example, from high frequency to low frequency in the vicinity of the resonant frequency of the vibration system including the ultrasonic transducer 13. The control circuit 40 obtains the current and voltage at that point from the first detection circuit 53 and obtains the frequency at which the phases of the current and the voltage coincide, that is, the resonant frequency of the vibration system. The control circuit 40 renders the obtained resonant frequency the initial value and uses the PLL even subsequent to that so as to cause the output frequency to follow the resonant frequency of the vibration system. Subsequently, the first grasping piece 15 is caused to vibrate at the resonant frequency using the PLL. Generally, since the temperature of the first grasping piece 15 gradually increases, the resonant frequency of the vibration system gradually decreases.

In step S104, the control circuit 40 determines whether or not the elapsed time T exceeds a predetermined first time threshold value Tth1. If the elapsed time T is not greater than the predetermined first time threshold value Tth1, the process in step S104 is repeated. That is, the process is in stand-by until the elapsed time T exceeds the first time threshold value Tth1. When the elapsed time T exceeds the first time threshold value Tth1, the process continues to step S105.

In step S105, the monitoring unit 42 of the control circuit 40 obtains a characteristic parameter X. Although the characteristic parameter X will be described later, it is, for example, the ultrasonic vibration amplitude of the ultrasonic transducer 13 represented by the output current to the ultrasonic transducer 13 or of the first grasping piece 15, the amount with which the handle 12 is being gripped, the amount of force with which the living tissue is being grasped by the end effector 7, the electrical impedance initial value of the living tissue being grasped by the end effector 7 etc.

The timing of obtaining the characteristic parameter X defined by the first time threshold value Tth1 may be any timing. For example, it may be after starting the PLL control. It may also be immediately after turning on the output switch.

In step S106, the threshold value setting unit 43 of the control circuit 40 evaluates the characteristic parameter X. If the characteristic parameter X is less than the predetermined second threshold value x2, the process continues to step S107. In step S107, the threshold value setting unit 43 of the control circuit 40 sets the value of the second time threshold value Tth2 to the value Tup that is greater than the standard value Tave. Subsequently, the process continues to step S110.

In step S106, if it is determined that the characteristic parameter X is equal to or greater than the predetermined second threshold value x2 and equal to or less than the predetermined first threshold value x1 (that is greater than the second threshold value x2), the process continues to step S108. In step S108, the threshold value setting unit 43 of the control circuit 40 sets the second time threshold value Tth2 to Tave, namely to the standard value set at the time of initialization. Subsequently, the process continues to step S110.

In step S106, if it is determined that the characteristic parameter X is greater than the predetermined first threshold value x1, the process continues to step S109. In step S109, the threshold value setting unit 43 of the control circuit 40 sets the value of the second time threshold value Tth2 to the value Tdown that is less than the standard value Tave. Subsequently, the process continues to step S110.

In step S110, the control circuit 40 determines whether the elapsed time T exceeds the second time threshold value Tth2 set in step S107, step S108 or step S109. If the elapsed time T is not greater than the second time threshold value Tth2, step S110 of the process is repeated. That is, until the elapsed time T exceeds the second time threshold value Tth2, the treatment is continued. If the elapsed time T exceeds the second time threshold value Tth2, the process continues to step S111.

In step S111, the output control unit 44 of the control circuit 40 performs output reduction. The output reduction operations are, for example, stopping the output of power from the first power supply 51 or lowering the output of power from the first power supply 51. The output reduction operations may be notifying the user, by the notification unit 64, that the elapsed time T has reached the second time threshold value Tth2. This operation may be, for example, outputting a display to a screen, outputting a notifying sound from a speaker, and the like. The output reduction operations may yet further be a combination of stopping or lowering the output power and notifying. After the process in step S111, the output control process ends.

Figure 5:
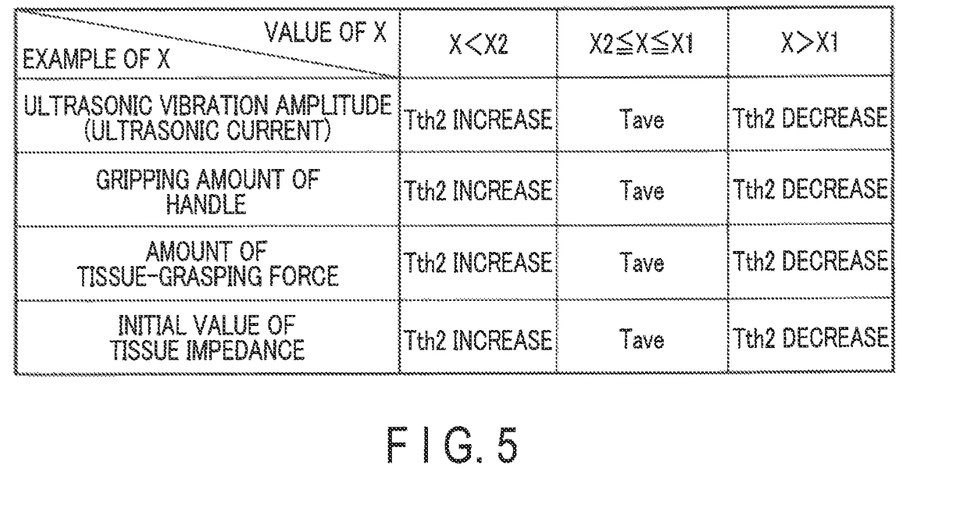
FIG. 5 is a view showing an example of a characteristic parameter according to the first embodiment, and an example of the relationship between a value of the characteristic parameter and a second time threshold value.

An example of the characteristic parameter X will be described. The characteristic parameter X is a parameter representing the situation of the treatment, and various parameters can be adopted as the characteristic parameter X. FIG. 5 shows an example of the characteristic parameter X and the relationship between the value of the characteristic parameter X and the second time threshold value Tth2. The relationship between the value of the characteristic parameter X and the second time threshold value Tth2 is stored in, for example, the storage medium 48.

The characteristic parameter X may be the amplitude of the ultrasonic vibration of the ultrasonic transducer 13 or the first grasping piece 15. Since this amplitude correlates with the current value supplied to the ultrasonic transducer 13, the characteristic parameter X may be the current value supplied to the ultrasonic transducer 13. As the amplitude of the ultrasonic vibration increases, the treatment of the living tissue grasped by the end effector 7 progresses more quickly. Therefore, the greater the amplitude of the ultrasonic vibration is, the shorter the second time threshold value Tth2 (namely the threshold value of the output duration) is set, and the less the amplitude of the ultrasonic vibration is, the longer it is set.

The characteristic parameter X may further be the amount with which the handle 12 is being gripped, obtained by the sensors 28 of the ultrasonic treatment tool 2. The greater the amount with which the handle 12 is being gripped, the stronger the living tissue is grasped by the first grasping piece 15 and the second grasping piece 16 of the end effector 7. The greater the end effector 7 grasps, the faster the treatment proceeds. Therefore, the greater the amount with which the handle 12 is being gripped is, the shorter the second time threshold value Tth2 (namely the output duration threshold value) is set, and the less the amount with which the handle 12 is being gripped, the longer it is set.

The force with which the living tissue is being grasped by the end effector 7 is not limited to being obtained by the amount with which the handle 12 is being gripped, but may be directly obtained by the sensors 28 of the ultrasonic treatment tool 2. That is, the characteristic parameter X may be the amount with which the living tissue is being grasped by the first grasping piece 15 and the second grasping piece 16 of the end effector 7, obtained by the sensors 28 of the ultrasonic treatment tool 2. The greater the amount of grasping force is, the shorter the second time threshold value Tth2 (namely the output duration of the threshold value) is set, and the less the amount of grasping force is, the longer it is set.

The characteristic parameter X may even further be the impedance value between the first grasping piece 15 and the second grasping piece 16 calculated from the current value and the voltage value detected by the second detection circuit 54, that is, it may be the impedance value of the living tissue being grasped by the end effector 7. This impedance value may, for example, be the initial value or various values representing the characteristics of the impedance value when it is varying. As the moisture content of the living tissue increases, the impedance value decreases. The greater the moisture content of the living tissue, the longer the treatment takes. Therefore, the lower the impedance value is, the longer the second time threshold value Tth2 (namely the threshold value of the output duration) is set, and the higher the impedance value is, the shorter it is set.

The second time threshold value Tth2 may be set to respective predetermined values according to the value of the characteristic parameter X being either: less than the predetermined second threshold value x2, equal to or greater than the second threshold value x2 and equal to or less than the first threshold value x1, or greater than the first threshold value x1. The second time threshold value Tth2 may further be set based on the relationship between the second time threshold value Tth2 and the characteristic parameter X determined in advance according to the value of the characteristic parameter X being either: less than the predetermined second threshold value x2, equal to or greater than the second threshold value x2 and equal to or less than the first threshold value x1, or greater than the first threshold value x1. That is, for example, even if the value of the characteristic parameter X is less than the predetermined second threshold value x2, the second time threshold value Tth2 may be configured to differ according to the value of the characteristic parameter X. Besides, although the above example scenario has been classified into three different scenarios depending on the value of the characteristic parameter X, the present example scenario may be classified into four or more.

As for any of the above-mentioned cases of the characteristic parameter X, there is a tendency to set the second time threshold value Tth2 to a lesser value the greater the value of the characteristic parameter X is, and to set the second time threshold value Tth2 to a greater value the less the characteristic parameter X is.

It should be noted that the characteristic parameter X is not limited to the above example, but that it may be any parameter as long as it represents a treatment situation of the ultrasonic treatment tool 2 and as long as it affects the treatment time. The second time threshold value Tth2 is appropriately set depending on whether the treatment time increases or decreases with the parameter.

In the treatment system 1 according to the first embodiment, when the treatment of the living tissue to be treated is completed and the tissue is incised or nearly incised, the ultrasonic vibration of the first grasping piece 15 is stopped or reduced, or a notice etc. to that effect is made. In this way, ultrasonic vibration of the first grasping piece 15 while the first grasping piece 15 and the pad member 21 of the second grasping piece 16 are in contact with each other is prevented. As a result, a lid is kept on abrasion and deformation of the pad member 21.

The determination, here, as to whether or not to stop the ultrasonic vibration of the first grasping piece 15 or the like is made based on the elapsed time from the start of the treatment. The threshold for determining the elapsed time, here, is set based on the characteristic parameter which reflects the situation of the treatment. The situation of the treatment varies depending on the type or characteristics of the targeted tissue, on how the user uses the ultrasonic treatment tool 2, and the like. Since the threshold value for the determination is set according to the situation of the treatment, the treatment system 1 according to the first embodiment can appropriately control the output according to the treatment situation.

Second Embodiment

A second embodiment and its differences from the first embodiment will be described. In this regard, same elements will be denoted by the same reference symbols and descriptions of same elements will be omitted. In the first embodiment, the characteristic parameter X is obtained once at a predetermined timing, and, based thereon, the second time threshold value Tth2 is set only once. In contrast to this, in the second embodiment, the value of the characteristic parameter X is obtained repeatedly, and, based thereon, the second time threshold value Tth2 is set sequentially. The other operations are the same as in the first embodiment.

Figure 6:
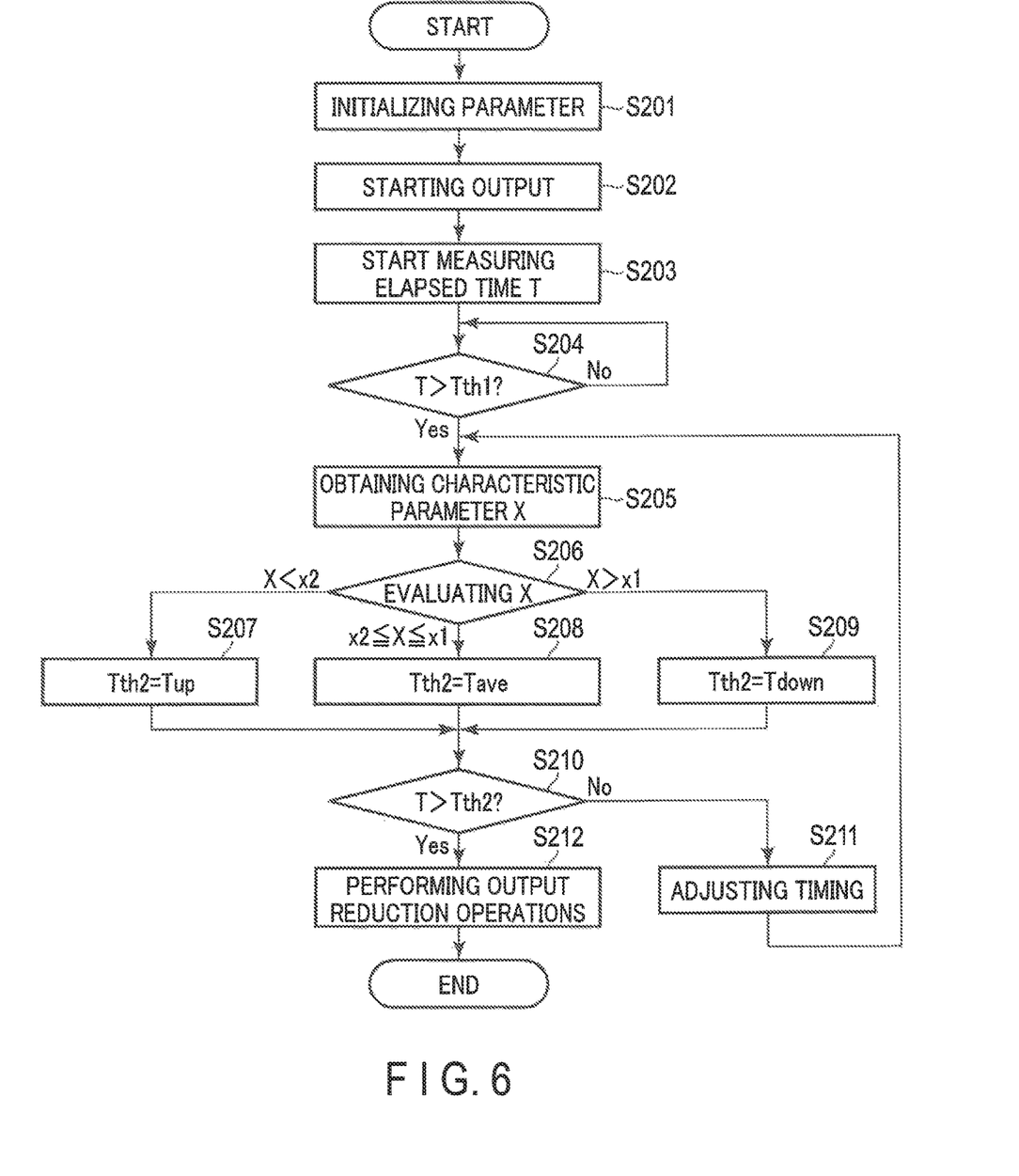
FIG. 6 is a schematic flowchart showing an example of an output control process according to a second embodiment.

The output control process according to the second embodiment will be described with reference to the flowchart shown in FIG. 6. The process related to steps S201 to S210 is similar to the process related to steps S101 to S110 of the output control process according to the first embodiment described with reference to FIG. 4. The following is a brief explanation.

In step S201, the control circuit 40 initializes the various parameters. In step S202, the output control unit 44 of the control circuit 40 causes the first power supply 51 to start outputting. In step S203, the clock unit 41 of the control circuit 40 starts measuring the elapsed time T of the treatment. In step S204, the control circuit 40 determines whether or not the elapsed time T exceeds the predetermined first time threshold value Tth1. If the elapsed time T exceeds the first time threshold value Tth1, the process continues to step S205.

In step S205, the control circuit 40 obtains the characteristic parameter X. In step S206, the control circuit 40 evaluates the characteristic parameter X. If the characteristic parameter X is less than the predetermined second threshold value x2, the control circuit 40 sets, in step S207, the value of the second time threshold value Tth2 to the value Tup greater than the standard value Tave. If it is determined that the characteristic parameter X is equal to or greater than the predetermined second threshold value x2 and equal to or less than the predetermined first threshold value x1 that is greater than the second threshold value x2, the control circuit 40 sets, in step S208, the second time threshold value Tth2 to the standard value Tave set at the time of initialization. If the characteristic parameter X is greater than the predetermined first threshold value x1, the control circuit 40 sets, in step S209, the value of the second time threshold value Tth2 to the value Tdown that is less than the standard value Tave set at the time of initialization.

In step S210, the control circuit 40 determines whether or not the elapsed time T exceeds the set second time threshold value Tth2. If the elapsed time T does not exceed the second time threshold value Tth2, the process continues to step S211. In step S211, the control circuit 40 waits for a predetermined interval period ΔT to adjust the timing. That is, the elapsed time T is T+ΔT. Therefore, ΔT may, for example, be approximately 10 microseconds to 10 seconds.

Subsequent to the process of step S211, the process returns to step S205. In this manner, the process from step S205 to step S211 is repeated until the elapsed time T exceeds the second time threshold value Tth2. That is, the control circuit 40 obtains the characteristic parameter X repeatedly, and resets the second time threshold value Tth2 based thereon.

If the elapsed time T exceeds the second time threshold value Tth2, the control circuit 40 performs the output reduction operations in step S212. Subsequently, the output control process ends.

In the second embodiment, the same effects as in the first embodiment are achievable. According to the second embodiment, the second time threshold value Tth2 for adjusting the timing of stopping the output of the ultrasonic treatment tool 2 and the like is adjusted, according to the characteristic parameter X changing constantly during the treatment. As a result, it is possible to perform an output reduction operations by which the output is stopped at the optimal timing and the like.

Third Embodiment

A third embodiment and its differences from the first embodiment will be described. In this regard, same elements will be denoted by the same reference symbols and descriptions of same elements will be omitted. In the first embodiment, the value of the characteristic parameter X is compared to a predetermined threshold value, and, according to the magnitude, the second time threshold value Tth2 is determined. In contrast to this, in the third embodiment, the second time threshold value Tth2 is determined as a function of the characteristic parameter X. The other operations are the same as in the first embodiment.

Figure 7:
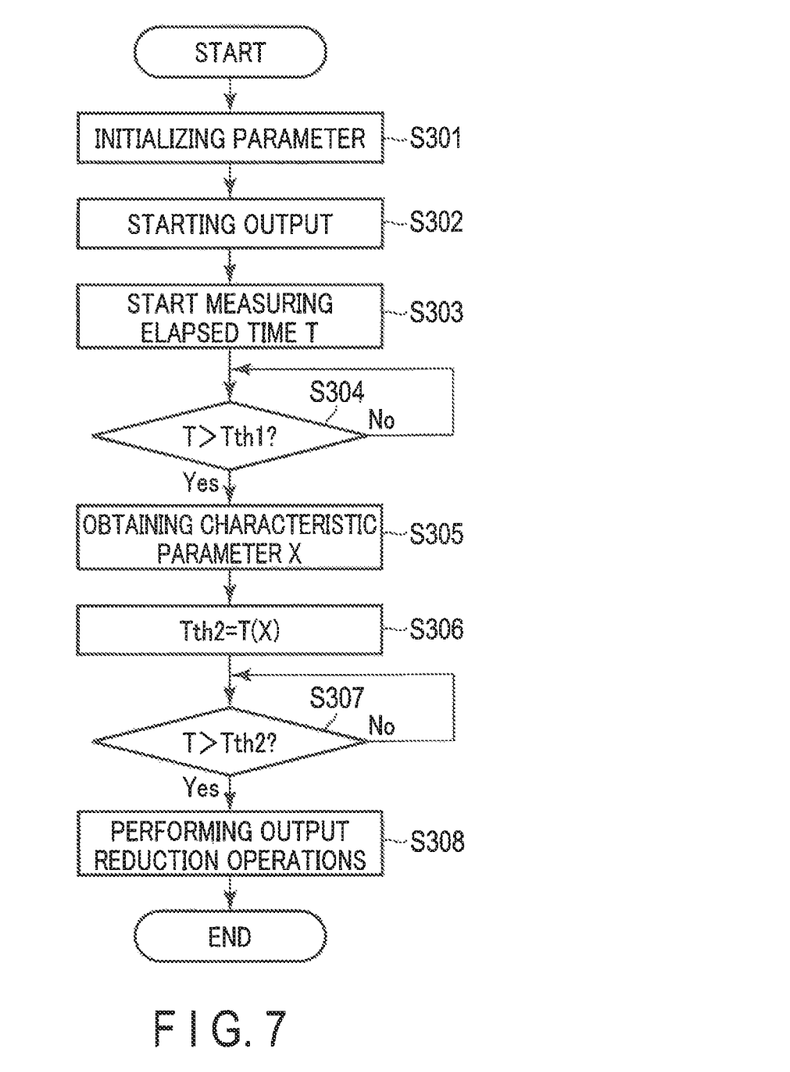
FIG. 7 is a schematic flowchart showing an example of an output control process according to a third embodiment.

The output control process according to the third embodiment will be described with reference to the flowchart shown in FIG. 7. The process related to steps S301 to S305 is the same as the process related to steps S101 to S105 of the output control process according to the first embodiment described with reference to FIG. 4. The following is a brief explanation.

In step S301, the control circuit 40 initializes the various parameters. In step S302, the output control unit 44 of the control circuit 40 causes the first power supply 51 to begin outputting. In step S303, the clock unit 41 of the control circuit 40 begins measuring the elapsed time T of the treatment. In step S304, the control circuit 40 determines whether or not the elapsed time T exceeds the predetermined first time threshold value Tth1. If the elapsed time T exceeds the first time threshold value Tth1, the process continues to step S305. In step S305, the control circuit 40 obtains the characteristic parameter X.

In step S306, the control circuit 40 determines the second time threshold value Tth2 based on the function Tth2=T(X) indicating the second time threshold value Tth2 with respect to the characteristic parameter X and the obtained characteristic parameter X.

Figure 8:
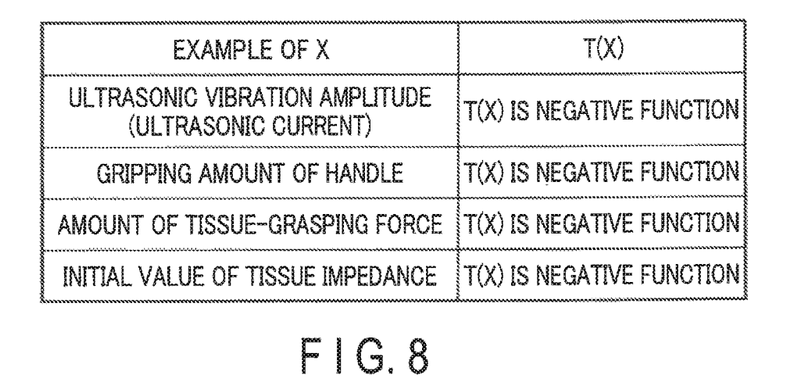
FIG. 8 is a view showing an example of a characteristic parameter according to the third embodiment and an example of the relationship between a value of the characteristic parameter and the second time threshold.

An example of the relationships between examples for the characteristic parameter X and the function T(X) is shown in FIG. 8. As in the case of the first embodiment, the characteristic parameter X is obtained by calculating the ultrasonic vibration amplitude (current value supplied to the ultrasonic transducer 13), the amount with which the handle 12 is being gripped, the amount of force with which the living tissue is being grasped by the end effector 7, the impedance value of the living tissue, and the like. Whichever of the above examples the characteristic parameter X is, the function T(X) is negative. The function T(X) may be of the n-th order, exponential, logarithmic, or any other.

In step S307, the control circuit 40 determines whether or not the elapsed time T exceeds the set second time threshold value Tth2. If the elapsed time T does not exceed the second time threshold value Tth2, the control circuit 40 continues the treatment. If the elapsed time T exceeds the second time threshold value Tth2, the control circuit 40 performs the output reduction operations in step S308. Subsequently, the output control process ends.

In the third embodiment, the same effects as in the first embodiment are achievable. According to the third embodiment, the second time threshold value Tth2 is appropriately adjusted based on the function T(X) and the characteristic parameter X. As a result, it is possible to perform an output reduction operations by which the output is stopped at the optimal timing and the like.

Fourth Embodiment

A fourth embodiment and its differences from the third embodiment will be described. In this regard, same elements will be denoted by the same reference symbols and descriptions of same elements will be omitted. In the third embodiment, the characteristic parameter X is obtained once at a predetermined timing, and, based thereon, the second time threshold value Tth2 is set only once. In contrast to this, in the fourth embodiment, as in the second embodiment, the value of the characteristic parameter X is obtained repeatedly, and, based thereon, the second time threshold value Tth2 is set sequentially. The other operations are the same as in the third embodiment.

Figure 9:
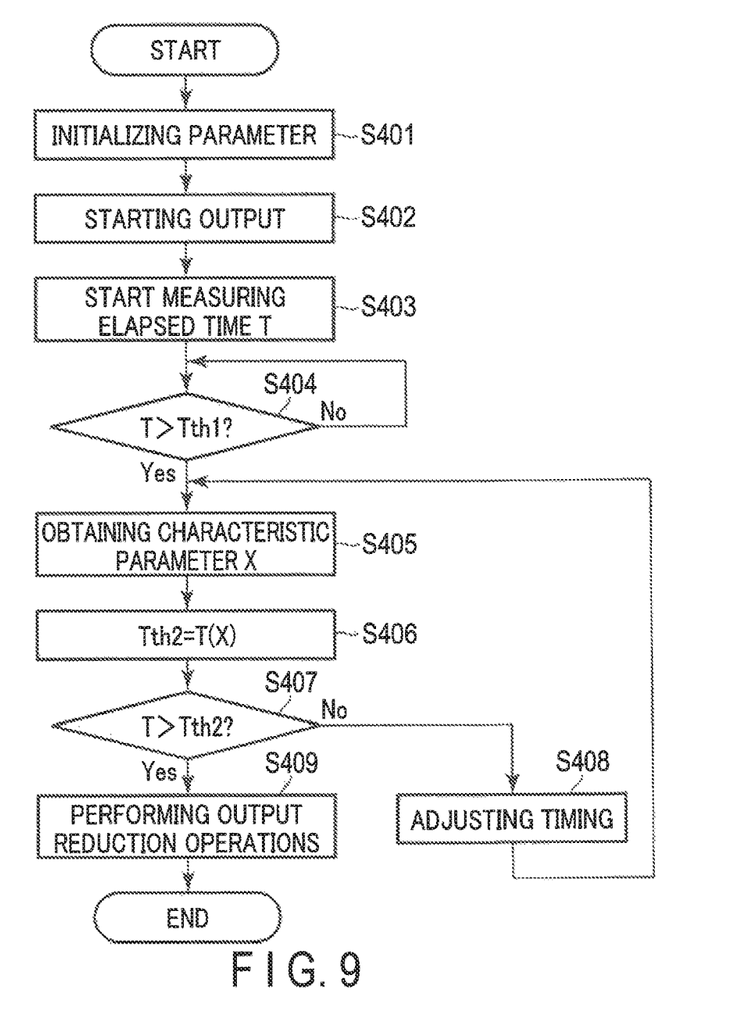
FIG. 9 is a schematic flowchart showing an example of an output control process according to a fourth embodiment.

The output control process according to the fourth embodiment will be described with reference to the flowchart shown in FIG. 9. The process related to steps S401 to S407 is the same as the process related to steps S301 to 3307 of the output control process according to the third embodiment described with reference to FIG. 7. The following is a brief explanation.

In step S401, the control circuit 40 initializes the various parameters. In step S402, the output control unit 44 of the control circuit 40 causes the first power supply 51 to begin outputting. In step S403, the clock unit 41 of the control circuit 40 begins measuring the elapsed time T of the treatment. In step S404, the control circuit 40 determines whether or not the elapsed time T exceeds the predetermined first time threshold value Tth1. If the elapsed time T exceeds the first time threshold value Tth1, the process continues to step S405. In step S405, the control circuit 40 obtains the characteristic parameter X. In step S406, the control circuit 40 determines the second time threshold value Tth2 based on the function Tth2=T(X) indicating the second time threshold value Tth2 with respect to the characteristic parameter X and the obtained characteristic parameter X.

In step S407, the control circuit 40 determines whether or not the elapsed time T exceeds the set second time threshold value Tth2. If the elapsed time T does not exceed the second time threshold value Tth2, the process continues to step S408. In step S408, the control circuit 40 waits for the predetermined interval period ΔT to adjust the timing. That is, the elapsed time T is T+ΔT. Subsequently, the process returns to step S405. In this manner, the control circuit 40 obtains the characteristic parameter X repeatedly, and, based thereon, resets the second time threshold value Tth2.

If the elapsed time T exceeds the second time threshold value Tth2, the control circuit 40 performs the output reduction operations in S409. Subsequently, the output control process ends.

In the fourth embodiment, the same effects as in the third embodiment are achievable. According to the fourth embodiment, the second time threshold value Tth2 for adjusting the timing of stopping the output of the ultrasonic treatment tool 2 or the like is adjusted according to the characteristic parameter X varying constantly during the treatment. As a result, it is possible to perform an output reduction operations by which the output is stopped at the optimal timing and the like.

Modifications

Several modifications of the above first to fourth embodiments will be described. These modifications may be applied in combination with each other as long as they do not contradict.

In the above embodiments, examples in which the output reduction operations have been performed according to the elapsed time T from the start of output of the ultrasonic treatment tool 2 have been described. However, the elapsed time T may not be measured from the start of output. The elapsed time T may, for example, be measured from the start of the above PLL control. The elapsed time T may also be measured from the time at which the obtained electrical impedance of the ultrasonic transducer 13 indicates the minimum value or the maximum value. That is, the output duration related to the time during which the first power supply 51 continued outputting may be measured as the elapsed time T.

The relationship between the characteristic parameter X and the second time threshold value Tth2 may be different for each model of the ultrasonic treatment tool 2. Therefore, the relationships between the characteristic parameter X and the second time threshold value Tth2 may be determined as follows. That is, in the storage medium 25 of the ultrasonic treatment tool 2, for example, identification information indicating the model of the ultrasonic treatment tool 2 is stored. Further, in the storage medium 48 of the energy control device 3, the relationships between the characteristic parameters X and the second time threshold values Tth2 for the models are stored. The control circuit 40 reads the model identification information from the storage medium 25 of the ultrasonic treatment tool 2 and uses the relationship between the characteristic parameter X and the second time threshold value Tth2 corresponding to the identification information.

It should be noted that, even if the model information of the ultrasonic treatment tool 2 is not stored in the storage medium 25, different resistors may, for example, be provided in the ultrasonic treatment tool 2 depending on the model of the ultrasonic treatment tool 2, and the energy control device 3 may discriminate the model of the ultrasonic treatment tool. 2 by obtaining the resistance value of the resistor at the time of connecting to the ultrasonic treatment tool 2. The relationship between the characteristic parameter X and the second time threshold value Tth2 may further be stored in the storage medium 25 of the ultrasonic treatment tool 2, and the control circuit 40 may read this information to set the second time threshold value Tth2.

Moreover, the energy control device 3 may be configured such that the type of output reduction operations according to the above embodiment or the presence or absence thereof can be switched based on instructions by the user input via the input unit 62.

Moreover, in the above embodiments, the case has been shown in which only a single second time threshold value Tth2 is set. However, two or more second time threshold values Tth2 may be set. For example, the energy control device 3 may be configured to reduce the output if the elapsed time T exceeds the first second time threshold value Tth21, and to stop the output if the elapsed time T exceeds the second time threshold value Tth22.

Further, in the above embodiments, a single parameter has been obtained as the characteristic parameter X, and, based thereon, the second time threshold value Tth2 has been determined. However, the present invention is not limited to this. A plurality of parameters may be obtained as the characteristic parameter X, and the second time threshold value Tth2 may be determined by a combination of these parameters.

It should be noted that in the above embodiments, the ultrasonic treatment tool 2 has been described as a tool performing treatment by the first grasping piece 15 that ultrasonically vibrate. However, the present invention is not limited to this. In the case where the energy control device 3 has the second power supply 52, the ultrasonic treatment tool 2 may also serve as a high-frequency treatment tool applying, in addition to the ultrasonic vibration, a high-frequency voltage between the first grasping piece 15 and the second grasping piece 16. The high-frequency treatment tool performs treatment with a Joule heat generated by current flowing through the tissue to be treated by applying a high-frequency current to the tissue. The ultrasonic treatment tool. 2 may further be a treatment tool provided with a heater on the first grasping piece 15 or the second grasping piece 16 for treating the tissue to be treated by both the heat from the heater and the ultrasonic vibration.

Additional advantages and modifications will readily occur to those skilled in the art. Therefore, the invention in its broader aspects is not limited to the specific details and representative embodiments shown and described herein. Accordingly, various modifications may be mA/De without departing from the spirit or scope of the general inventive concept as defined by the appended claims and their equivalents.

What is claimed is:

1. An energy control device for an ultrasonic treatment tool, the energy control device comprising:
    a first power supply configured to supply electric power to an ultrasonic transducer of the ultrasonic treatment tool that is configured to generate an ultrasonic vibration from the supplied electric power, the ultrasonic treatment tool further including an end effector configured to perform a treatment by transmitting the ultrasonic vibration; and
    a circuit configured to:
       measure a duration of electric power output by the first power supply,
       monitor a predetermined characteristic parameter representative of a status of the treatment by repeatedly obtaining measurements of the predetermined characteristic parameter,
       set and reset a time threshold value based on the repeatedly obtained measurements of the predetermined characteristic parameter until the duration of the electric power output exceeds the time threshold value, and
       perform at least one of the following when the duration of the electric power output exceeds the time threshold value: stopping or reducing the output of electric power from the first power supply to the ultrasonic transducer, and notifying a user that the duration of electric power output has exceeded the time threshold value.

2. The energy control device according to claim 1, wherein the circuit is configured to obtain a current value of the electric power supplied to the ultrasonic transducer as the characteristic parameter.

3. The energy control device according to claim 2, wherein the circuit is configured to:
    set the time threshold value to be a preset standard value if the current value is equal to or greater than a second predetermined current threshold value and equal to or less than a first predetermined current threshold value greater than the second predetermined current threshold value,
    set the time threshold value to be greater than the preset standard value if the current value is less than the second predetermined current threshold value, and
    set the time threshold value to be less than the preset standard value if the current value is greater than the first predetermined current threshold value.

4. The energy control device according to claim 2, wherein the circuit is configured to set the time threshold value based on a function with respect to the current value.

5. The energy control device according to claim 1, further comprising a second power supply configured to supply an electric power between a pair of graspers comprised by the end effector of the ultrasonic treatment tool,
    wherein the circuit is configured to obtain, as the characteristic parameter, an impedance value related to the electric power supplied between the pair of graspers.

6. The energy control device according to claim 5, wherein the circuit is configured to:
    set the time threshold value to be a preset standard value if the impedance value is equal to or greater than a second predetermined impedance threshold value and equal to or less than a first predetermined impedance threshold value greater than the second predetermined impedance threshold value,
    set the time threshold value to be greater than the preset standard value if the impedance value is less than the second predetermined impedance threshold value, and
    set the time threshold value to be less than the preset standard value if the impedance value is greater than the first predetermined impedance threshold value.

7. The energy control device according to claim 5, wherein the circuit is configured to set the time threshold value based on a function with respect to the impedance value.

8. The energy control device according to claim 1, wherein
    the circuit is configured to obtain, as the characteristic parameter, an amount of displacement of a handle that is disposed on the ultrasonic treatment tool and is movable to open and close a pair of graspers comprised by the end effector, the amount of displacement being detected by a sensor comprised by the ultrasonic treatment tool.

9. The energy control device according to claim 8, wherein the circuit is configured to:
    set the time threshold value to be a preset standard value if the amount of displacement is equal to or greater than a second predetermined displacement threshold value and equal to or less than a first predetermined displacement threshold value greater than the second predetermined displacement threshold value,
    set the time threshold value to be greater than the preset standard value if the amount of displacement is less than the second predetermined displacement threshold value, and
    set the time threshold value to be less than the preset standard value if the amount of displacement is greater than the first predetermined displacement threshold value.

10. The energy control device according to claim 8, wherein the circuit is configured to set the time threshold value based on a function with respect to the amount of displacement.

11. The energy control device according to claim 1, wherein
the circuit is configured to obtain, as the characteristic parameter, a grasping force of a pair of graspers comprised by the end effector, the grasping force being detected by a sensor comprised by the ultrasonic treatment tool.

12. The energy control device according to claim 11, wherein the circuit is configured to:
set the time threshold value to be a preset standard value if the grasping force is equal to or greater than a second predetermined grasping force threshold value and equal to or less than a first predetermined grasping force threshold value greater than the second predetermined grasping force threshold value,
set the time threshold value to be greater than the preset standard value if the grasping force is less than the second predetermined grasping force threshold value, and
set the time threshold value to be less than the preset standard value if the grasping force is greater than the first predetermined grasping force threshold value.

13. The energy control device according to claim 11, wherein the circuit is configured to set the time threshold value based on a function with respect to the grasping force.

14. The energy control device according to claim 1, wherein the circuit is configured to:
monitor a plurality of characteristic parameters by repeatedly obtaining measurements of the plurality of characteristics parameters, and
set and reset the time threshold value based on the repeatedly obtained measurements of the plurality of parameters.

15. A treatment system comprising:
the energy control device according to claim 1; and
the ultrasonic treatment tool connectable to the energy control device.

16. The treatment system according to claim 15, wherein
the end effector comprises a first grasper configured to transmit ultrasonic vibrations and a second grasper configured to open and close with respect to the first grasper, and
the second grasper comprises a pad member configured to contact the first grasper when the first grasper and the second grasper are closed.

17. The treatment system according to claim 15, wherein
the ultrasonic treatment tool comprises a storage medium configured to store a relationship between the characteristic parameter and the time threshold value, and
the circuit is configured to: read the relationship between the characteristic parameter and the time threshold value from the storage medium, and set the time threshold value based on the relationship when the ultrasonic treatment tool is connected to the energy control device.

18. The treatment system according to claim 15, wherein:
the ultrasonic treatment tool comprises a first storage medium in which identification information is stored,
the energy control device comprises a second storage medium in which a correspondence relationship between the identification information and a relationship between the characteristic parameter and the time threshold value is stored, and
the circuit is further configured to: (i) read the identification information from the first storage medium, (ii) read the correspondence relationship between the identification information and the relationship between the characteristic parameter and the time threshold value from the second storage medium, and (iii) set the time threshold value based on the correspondence relationship.

19. The treatment system according to claim 15, wherein:
the end effector comprises a pair of graspers,
the ultrasonic treatment tool further comprises:
a handle moveable to open and close the pair of graspers, and
a sensor configured to detect an amount of displacement of the handle, and
the circuit is configured to obtain the amount of displacement of the handle as the characteristic parameter.

20. The treatment system according to claim 15, wherein:
the end effector comprises a pair of graspers,
the ultrasonic treatment tool further comprises a sensor configured to detect a grasping force of the pair of graspers, and
the circuit is configured to obtain the grasping force as the characteristic parameter.

* * * * *